United States Patent [19]

Georgiev et al.

[11] Patent Number: 4,683,311

[45] Date of Patent: Jul. 28, 1987

[54] SPIRO[ISOXAZALIDINE-3,2'-TRICY-CLO[3.3.1.1[3,7]] DECANES]

[75] Inventors: Vassil S. Georgiev, Rochester; George B. Mullen, Avon, both of N.Y.

[73] Assignee: Pennwalt Corporation, Philadelphia, Pa.

[21] Appl. No.: 821,292

[22] Filed: Jan. 22, 1986

[51] Int. Cl.[4] .......................................... C07D 261/02
[52] U.S. Cl. .................................................... 548/240
[58] Field of Search ........................................ 548/240

[56] References Cited

U.S. PATENT DOCUMENTS 4,254,128  3/1981  Weiner et al. ..................... 564/459
4,283,422  8/1981  Alsumi et al. ..................... 564/459

Primary Examiner—Donald G. Daus
Assistant Examiner—Barbara Cassatt

[57] ABSTRACT

The compounds are of the class of adamantanyl isoxazolidine derivatives useful as anti-inflammatory, antihypoxia, antimicrobial and anticonvulsant agents. Exempliary of a species of the compounds is 2 methyl-5-n-hexyl-spiro[isoxazolidin-3,2'-tricyclo[3.3.1.1[3,7]] decane].

20 Claims, No Drawings

SPIRO[ISOXAZALIDINE-3,2'-TRICYCLO[3.3.1.1$^{3,7}$]DECANES]

FIELD OF THE INVENTION

This invention relates to new adamantanyl isoxazolidine derivatives. More particularly, it relates to derivatives of spiro[isoxazolidine-3,2'-tricyclo[3.3.1.1$^{3,7}$]decane]. Some of these compounds, when tested, were found to have anti inflammatory activity against carrageenan induced edema in a laboratory animal model and, in some instances, antimicrobial (N. gonorrhoeae), antihypoxia, analgesic and anticonvulsant activity in animal testing.

STATEMENT OF THE INVENTION

This invention includes derivatives of a spiro [isoxazolidine-3,2'-tricyclo[3.3.1.1$^{3,7}$]decane]having the structural formula

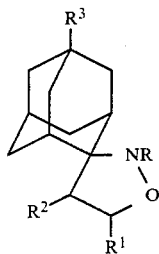

wherein R is a lower alkyl group; R$^1$ is a substituent selected from the group consisting of C$_1$-C$_{24}$ alkyl, an amino(C$_1$-C$_4$ alkyl), a carboxyl, a phenyl, a (C$_1$-C$_4$ alkoxy)carbonyl, a (halogenated acetamido)C$_1$-C$_4$ alkyl, a hydroxy(C$_1$-C$_4$ alkyl), an aminocarbonyl, a (C$_1$-C$_4$ alkylamino)carbonyl, an [(aminocarbonyl)amino]C$_1$-C$_4$ alkyl, a [[(C$_1$-C$_4$ alkylamino)carbonyl]amino]C$_1$-C$_4$ alkyl, a [[(phenylamino)thiocarbonyl]amino]C$_1$-C$_4$ alkyl, a (C$_1$-C$_{24}$ alkanoyloxy)C$_1$-C$_4$ alkyl and a (C$_1$-C$_{24}$ alkanoylamino)C$_1$-C$_4$ alkyl; R$^2$ is hydrogen or a lower alkoxycarbonyl; and R$^3$ is hydrogen or hydroxy.

DETAILED DESCRIPTION OF THE INVENTION

The compounds of this invention are derivatives of spiro[isoxazolidine-3,2'-tricyclo[3.3.1.1$^{3,7}$]decane]of the structural formula as set forth above.

The R substituent of the formula is preferably a lower alkyl group (C$_1$ to about C$_8$ alkyl), more preferably an alkyl group having less than 5 carbon atoms. R$^1$ is preferably a C$_1$-C$_{24}$ alkyl, most preferably a C$_1$-C$_7$ alkyl or C$_{15}$-C$_{17}$ alkyl; an aminoalkyl having less than 5 carbons, most preferably aminomethyl; carboxyl; phenyl; a C$_1$-C$_4$ alkoxycarbonyl; a (halogenated acetamido)C$_1$-C$_4$ alkyl, for example, (trifluoroacetamido)methyl; a hydroxyalkyl having less than 5 carbons, most preferably hydroxymethyl; aminocarbonyl; (C$_1$-C$_4$ alkylamino) carbonyl; [(aminocarbonyl)amino]C$_1$-C$_4$ alkyl, most preferably [(aminocarbonyl)amino]methyl; [(C$_1$-C$_4$ alkylamino-carbonyl) amino]C$_1$-C$_4$ alkyl, most preferably [(methylamino-carbonyl) amino]methyl; [[(phenylamino)thiocarbonyl]amino]C$_1$-C$_4$ alkyl, most preferably [[(phenylamino)thiocarbonyl]amino]methyl; (C$_1$-C$_{24}$ alkanoyloxy) C$_1$-C$_4$ alkyl, for example (n-hexadecanoyloxy) methyl; and a (C$_1$-C$_{24}$ alkanoylamino)C$_1$-C$_4$ alkyl, for example, (n-hexadecanamido)methyl. R$^2$ is hydrogen or a lower alkoxycarbonyl, preferably where the alkyl group has less than 5 carbon atoms, and R$^3$ is hydrogen or a hydroxy group.

In general, the adamantanyl isoxazolidine derivatives of this invention are prepared by condensing 2-adamantanone in an inert atmosphere with an appropriate N-substituted hydroxylamine, usually dissolved in an inert organic solvent, to provide the corresponding adamantyl nitrone. The latter compound is then reacted with a substituted olefin and undergoes 1,3-dipolar cycloaddition to provide one of the adamantanyl isoxazolidine derivatives of this invention.

EXAMPLES

The following examples demonstrate the preparation of representative compounds of this invention.

EXAMPLE 1

2-Methyl-5-n-hexyl-spiro[isoxazolidine-3,2'-tricyclo [3.3.1.1$^{3,7}$]decane]was prepared as follows:

Under a nitrogen atmosphere, 18.03 g (0.12 mole) of 2-adamantanone and 10.34 g (0.13 mole) of N-methylhydroxylamine were dissolved in 300 ml of absolute ethanol. Sodium bicarbonate (10.99 g, 0.13 mole) was added and the resulting suspension refluxed for 3 hours. Upon cooling to room temperature, the solvent was removed in vacuo, 250 ml of toluene were added, and the suspension was filtered. C$_6$H$_{13}$CH=CH$_2$ (1-octene) (48 ml, 2.5 equiv) was added to the filtrate and the solution was refluxed under nitrogen for 40 hours. Removal of the solvent gave a yellow oil which crystallized from ethyl ether saturated with hydrogen chloride, giving 26.25 g (67%) of the hydrochloride salt of 2-methyl-5-n-hexyl-spiro[isoxazolidine-3,2'-tricyclo[3.3.1.1$^{3,7}$]decane]as a white solid. Recrystallization from ethyl acetate gave an analytical sample, m.p. 134–136° C.

Anal. Calcd. for C$_{19}$H$_{34}$ClNO:C, 69.59; H, 10.45; N, 4.27; Cl, 10.81. Found: C, 69.21; H, 10.84; N, 4.22; Cl, 10.66.

This compound showed antihypoxic and anticonvulsant activity at a dosage level of 200 mg/kg.

EXAMPLE 2

2-Methyl-5-methoxycarbonyl-spiro[isoxazolidine-3,2'-tricyclo [3.3.1.1$^{3,7}$]decane]was prepared in accordance with the procedure of Example 1 except that the substituted olefin was

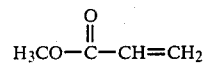

(methyl acrylate). Recrystallization from methanol gave an analytical sample, m.p. 166–170° C.

Anal. Calcd. for C$_{15}$H$_{24}$ClNO$_3$: C; 59.69; H,8.02; N,4.64;Cl, 11.75. Found: C,59.77; H,8.30; N,4.66; Cl,12.26.

This compound showed antimicrobial (N.gonorrhoeae), anti-inflammatory and antihypoxic activity at dosage levels ranging from 50 to 200 mg/kg.

EXAMPLE 3

2-Methyl-5-methyl-4-methoxycarbonyl spiro[isoxazolidine-3, 2'-tricyclo[3.3.1.1$^{3,7}$]decane]was prepared in accordance with the procedure of Example 1 except that the substituted olefin

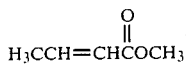

was (methyl crotonate). Recrystallization from methanol gave an analytical sample, m.p. 127–129° C.

Anal. Calcd. for $C_{16}H_{25}NO_3$: C,68.79; H,9.02; N,5.01. Found: C,69.06; H,9.25; N,4.98. This compound showed anti-inflammatory activity at 50 mg/kg dosage.

EXAMPLE 4

2-Methyl-5-hydroxymethyl-spiro[isoxazolidine-3,2'-tricyclo [3.3.1.1$^{3,7}$]decane]was prepared in accordance with the procedure of Example 1 except that the substituted olefin was $HOH_2C-CH=CH_2$ (allyl alcohol). Recrystallization from methanol gave an analytical sample, m.p. 93–96° C.

Anal. Calcd. for $C_{14}H_{23}NO_2$: C,70.35; H,9.77; N,5.90. Found: C,71.38; H,9.69; N,5.92. This compound showed anticonvulsant activity at 190 mg/kg dosage.

EXAMPLE 5

2-Methyl-5-(aminocarbonyl)-spiro[isoxazolidine-3,2'-tricyclo[3.3.1.1$^{3,7}$]decane]was prepared in accordance with the procedure of Example 1 except that the substituted olefin was

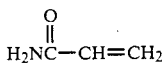

(acrylamide). Recrystallization from methanol gave an analytical sample, m.p. 182–183° C.

Anal. Calcd. for $C_{14}H_{22}N_2O_2$: C,67.17; H,8.86; N,11.19. Found: C,67.38; H,9.23; N,11.25. This compound showed antihypoxic activity at 200 mg/kg dosage.

EXAMPLE 6

2-Ethyl-5-phenyl-spiro[oxazolidine-3,2'-tricyclo[3.3.1.1$^{3,7}$]decane was prepared in accordance with the procedure of Example 1 except that the substituted olefin was $C_6H_5CH=CH_2$ (styrene) and the N-methylhydroxylamine was replaced with N-ethylhydroxylamine. Recrystallization from methanol gave an analytical sample, m.p. 91–94° C.

Anal. Calcd. for $C_{20}H_{27}NO$: C,80.76; H,9.15; N,4.71. Found C,80.79; H,9.30; N,4.67. This compound showed anticonvulsant activity at 135 mg/kg.

EXAMPLE 7

2-Methyl-5-(trifluoroacetamido)methyl-spiro[isoxazolidine-3,2'-tricyclo[3.3.1.1$^{3,7}$]decane]was prepared in accordance with the procedure of Example 1 except that the substituted olefin was

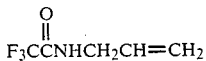

(N-allyl trifluoroacetamide). Recrystallization from methanol gave an analytical sample, m.p. 144–147° C.

Anal. Calcd. for $C_{16}H_{23}F_3N_2O_2$: C,57.82; H,6.97; N,8.43; F,17.15. Found: C,57.89; H,7.02; N,8.43; F,17.26. This compound showed antihypoxic activity at 100 mg/kg.

EXAMPLE 8

2-Methyl-spiro[isoxazolidine-3,2'-tricyclo[3.3.1.1$^{3,7}$]decane]-5-carboxylic acid was prepared as follows:

Aqueous sodium hydroxide (1N, 4.0 ml) was added to a solution of 1.01 g (3.8 mmoles) of the compound prepared in Example 2 in 20 ml of dioxane. The reaction was stirred for 45 min, then the solvent was removed. The residue was dissolved in water and acidified to pH 1.0 with dilute hydrochloric acid; a precipitate formed and was collected to give 0.73 g (76%) of 2-methyl-spiro[isoxazolidine-3,2'-tricyclo [3.3.1.1$^{3,7}$]decane]-5-carboxylic acid. Recrystallization from isopropanol gave an analytical sample, m.p. 156–159° C. (decomp).

Anal. Calcd. for $C_{14}H_{21}NO_3$: C, 66.91; H, 8.42; N, 5.57. Found: C, 66.82; H, 9.07; N, 5.54. This compound shows antihypoxic activity at 100 mg/kg.

EXAMPLE 9

2-Methyl-5-(aminomethyl)-spiro[isoxazolidine-3,2'-tricyclo [3.3.1.1$^{3,7}$]decane]was prepared as follows:

To a solution of 16.62 g (0.050 mole) of the compound of Example 7 in 200 ml of ethanol was added 60 ml of 1N aqueous sodium hydroxide. After stirring for 3 hours, the reaction was diluted with water and extracted with methylene chloride. The organic layer was washed with water, dried and evaporated. The remaining oil was crystallized from ethanol saturated with HCl gas as the dihydrochloride salt of 2-methyl-5-(aminomethyl)-spiro-[isoxazolidine-3,2'-tricyclo [3.3.1.1$^{3,7}$]decane]. Yield:12.74 g (82%), m.p. 209–229° C. (decomp).

Anal. Calcd. for $C_{14}H_{26}Cl_2N_2O$: C, 54.37; H, 8.47; N, 9.06; Cl, 22.93. Found: C, 54.44; H, 8.88; N, 9.06; Cl, 22.66. This compound shows antihypoxic activity at 100 mg/kg.

EXAMPLE 10

2-Methyl-5-[[(methylamino)carbonyl]amino]methyl-spiro ]isoxazolidine-3,2'-tricyclo[3.3.1.1$^{3,7}$]decane]was prepared as follows:

Under a nitrogen atmosphere, methyl isocyanate (1.5 ml, 1.5 equiv) was added to a solution of 3.90 g (16.5 moles) of a compound prepared in accordance with Example 9 in 150 ml of ether, at 5° C. After 2½ hours, the precipitate was collected and crystallized from methanol; Yield: 3.55 g (73%), m.p. 176–180° C.

Anal. Calcd. for $C_{16}H_{27}N_3O_2$: C, 65.50; H, 9.27; N, 14.32. Found: C, 65.36; H, 9.58; N, 14.26. This compound showed anticonvulsant activity at 350 mg/kg dosage.

EXAMPLE 11

2-Methyl-5-[[(phenylamino)thiocarbonyl]amino]-methyl-spiro [isoxazolidine-3,2'-tricyclo[3.3.1.1$^{3,7}$]decane]was prepared as follows:

Under a nitrogen atmosphere, 3.3 ml (1.1 equiv) of phenylisothiocyanate was added to a solution of 5.91 g (25.0 mmoles) of a compound prepared in accordance with Example 9 in 100 ml of ether. The reaction mixture was stirred for 1 hour at 5° C., then for 2 hours at room temperature. The product was collected by filtration. Yield: 9.03 g (97%). Recrystallization from ethyl acetate gave an analytical sample, m.p. 186–189° C. (decomp).

Anal. Calcd. for $C_{21}H_{29}N_3OS$: C, 67.89; H, 7.81; N, 11.31. Found: C, 67.99; H, 7.96; N, 11.37. This compound showed anticonvulsant activity at 400 mg/kg.

EXAMPLE 12

2-Methyl-5-(n-hexadecanamido)methyl-spiro[isoxazolidine-3,2′-tricyclo [3.3.1.1$^{3,7}$]decane]was prepared as follows:

Under a nitrogen atmosphere, 5.91 g (25.0 mmoles) of a compound prepared in accordance with Example 9 and 5.2 ml (1.5 equiv) of triethylamine were dissolved in 100 ml of dry tetrahydrofuran. The solution was cooled in an ice bath and then 7.56 g (1.1 equiv) of palmitoyl chloride was added dropwise over 10 min. The resulting suspension was stirred for 1 hour at 5° C., for 2 hours at room temperature, then poured into ice-water and extracted with methylene chloride. The organic layer was dried and the solvent removed. Crystallization from ethyl acetate gave the desired product as white granules. Yield: 9.99 g (84%), m.p. 74–76° C.

Anal. Calcd. for $C_{30}H_{54}N_2O_2$: C, 75.90; H, 11.46; N, 5.90. Found: C, 75.85; H. 11.54; N, 5.78. This compound showed antihypoxic activity at 25 mg/kg dosage.

EXAMPLE 13

2-Methyl-5-(n-hexadecanoyloxy)methyl-spiro[isoxazolidine-3,2′-tricyclo[3.3.1.1$^{3,7}$]decane]was prepared using the compound of Example 4 as follows:

palmitoyl chloride (5.90 g., 0.0215 mole) was added to a solution of 2-methyl-5-(hydroxymethyl)-spiro-[isoxazolidine-3,2′-tricyclo [3.3.1.1$^{3,7}$]decane](4.75 g, 0.0200 mole) and triethylamine (3.0 ml, 0.0216 mole) in 50 ml of dry tetrahydrofuran, while stirring at 10° C. under a nitrogen atmosphere. The resulting suspension was then stirred for 20 hours at room temperature, poured into 150 ml of ice-water and extracted with 200 ml of ether. The organic layer was dried over anhydrous magnesium sulfate, filtered and the solvent removed in vacuo, leaving a yellow oil. Flash chromatography on silica gel, using 98:2 methylene chloride/methanol as eluant, gave, after crystallization from pentane, 6.64 g (70%) of the desired product as white granules, m.p. 38–44° C.; calculated for $C_{30}H_{53}NO_3$: C,75.74; H, 11.23; N, 2.94. Found: C, 76.13; H, 11.53; N, 2.75. This compound was found to have antihypoxic activity at 100 mg/kg dosage.

EXAMPLE 14

Methyl 5$^1$-hydroxy-2-methyl spiro[isoxazolidine-3-2′-tricyclo [3.3.1.1$^{3,7}$]decane]-5-carboxylate was prepared as follows:

1-Hydroxytricyclo[3.3.1.1$^{3,7}$]decan-4-one was first prepared from tricyclo[3.3.1.1$^{3,7}$]decane]-2-one by the procedure of L. Vodicka et al. *Sb. Vys. Sk. Chem. Technol. Praz., Technol.* Paliv 1978 D39, 357. A suspension of 1-hydroxy-tricyclo [3.3.1.1$^{3,7}$]decane-4-one (3.85 g, 0.0232 mole), N-methylhydroxylamine hydrochloride (2.00 g, 1.01 equiv.) and sodium bicarbonate in 100 ml of ethanol was refluxed for 2 hours under a nitrogen atmosphere. Upon cooling to room temperature, the suspension was filtered and the solvent removed in vacuo. The oily residue was dissolved in 100 ml of benzene, 4.0 ml (0.044 moles) of methyl acrylate was added, and the solution was refluxed for 16 hours under a nitrogen atmosphere. The reaction was cooled to room temperature, the solvent removed in vacuo, and the residual oil was flash chromatographed on silica gel, using ethyl acetate as the eluant, to give 2.77 g (42%) of the product as an oil (mixture of isomers); calculated for $C_{15}H_{23}NO_4$: C, 64.04; H, 8.24; N, 4.98. Found, C, 63.98; H, 8.06; N, 4.18.

This compound was found to have anti-inflammatory activity at 50 mg/kg dosage.

EXAMPLE 15

The following alkanes:
(a) 1-hexene,
(b) 1-decene,
(c) 1-dodecene
(d) 1-hexadecene,
(e) 1-octadecene,
(f) 1-eicosene,
(g) and styrene;
are used in the procedure of Example 1 to replace 1-octene to prepare the following compounds:
(a) 2-methyl-5-n-butyl-spiro[isoxazolidine-3,2′-tricyclo [3.3.1.1$^{3,7}$]decane], m.p. 145–148° C.
(b) 2-methyl-5-n-octyl-spiro[isoxazolidine-3,2′-tricyclo [3.3.1.1$^{3,7}$]decane], m.p. 103-106° C.
(c) 2-methyl-5-n-decyl-spiro[isoxazolidine-3,2′-tricyclo [3.3.1.1$^{3,7}$]decane], m.p. 129-134° C.
(d) 2-methyl-5-n-tetradecyl-spiro[isoxazolidine-3,2′-tricyclo[3.3.1.1$^{3,7}$]decane], m.p. 111–114° C.
(e) 2-methyl-5-n-hexadecyl-spiro[isoxazolidine-3,2′-tricyclo[3.3.1.1$^{3,7}$]decane], m.p. 108–111° C.
(f) 2-methyl-5-n-octadecyl-spiro[isoxazolidine-3,2′-tricyclo[3.3.1.1$^{3,7}$]decane], m.p. 110–113° C.
(g) 2-methyl-5-phenyl-spiro[isoxazolidine-3,2′-tricyclo [3.3.1.1$^{3,7}$]decane], m.p. 85–88° C.

Of the above compounds, (a), (b), (e), and (g) were found to have anti-convulsant and antihypoxic activity, (a) had antimicrobial activity, and (d) had anti-inflammatory activity.

We claim:

1. A spiro [isoxazolidine -3,2′-tricyclo[3.3.1.1.$^{3,7}$]decane]compound having the structural formula

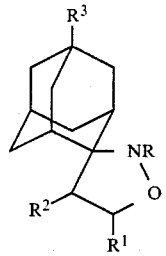

wherein R is a $C_1$–$C_4$ alkyl group; $R^1$ is a substituent selected from the group consisting of $C_1$–$C_{24}$ primary alkyl, an amino $C_1$–$C_4$ alkyl, a carboxyl, a phenyl, a $C_1$–$C_4$ alkoxy carbonyl, a (trifluoroacetamido)$C_1$–$C_4$ alkyl, a hydroxy $C_1$–$C_4$ alkyl, an aminocarbonyl, a ($C_1$–$C_4$ alkylamino) carbonyl, an [(aminocarbonyl)amino]$C_1$–$C_4$ alkyl, a [[($C_1$–$C_4$ alkylamino)carbonyl]amino]$C_1$–$C_4$ alkyl, a [[(phenylamino)thiocarbonyl]amino]$C_1$–$C_4$ alkyl, a ($C_1$–$C_{24}$ alkanoyloxy)$C_1$–$C_4$ alkyl and a ($C_1$–$C_{24}$ alkanoylamino) $C_1$–$C_4$ alkyl; $R^2$ is hydrogen or a $C_1$–$C_4$ alkoxycarbonyl; and $R^3$ is hydrogen or hydroxy, and the hydrochloride salt of said compound.

2. The compound of claim 1 wherein R is an alkyl having less than 5 carbon atoms.

3. The compound of claim 2 wherein $R^2$ and $R^3$ are hydrogen.

4. The compound of claim 2 wherein $R^1$ is $C_1$–$C_{24}$ alkyl.

5. The compound of claim 2 wherein $R^1$ is a $C_1$–$C_4$ alkoxycarbonyl.

6. The compound of claim 5 wherein $R^1$ is methoxycarbonyl.

7. The compound of claim 2 wherein $R^1$ is a hydroxy($C_1$–$C_4$ alkyl).

8. The compound of claim 7 wherein $R^1$ is hydroxymethyl.

9. The compound of claim 2 wherein $R^1$ is $C_1$–$C_4$ alkyl, $R^2$ is $C_1$–$C_4$ alkoxycarbonyl and $R^3$ is hydrogen.

10. The compound of claim 9 wherein $R^1$ is methyl and $R^2$ is methoxycarbonyl.

11. The compound of claim 2 wherein $R^1$ is a ($C_1$–$C_{24}$ alkanoyloxy)$C_1$–$C_4$ alkyl.

12. The compound of claim 2 wherein $R^1$ is a ($C_1$–$C_{24}$ alkanoylamino)$C_1$–$C_4$ alkyl.

13. The compound of claim 2 wherein $R^1$ is phenyl.

14. The compound of claim 2 wherein $R^1$ is aminocarbonyl.

15. The compound of claim 2 wherein $R^1$ is carboxyl.

16. The compound of claim 4 wherein $R^2$ is hydrogen and $R_3$ is hydroxy.

17. The compound of claim 15 wherein $R^1$ is methoxycarbonyl.

18. The compound of claim 1 in the form of its hydrochloride salt.

19. The compound of claim 18 wherein R is an alkyl group having less than 5 carbon atoms, $R^1$ is methoxycarbonyl and $R^2$ and $R^3$ are hydrogen.

20. The compound of claim 18 wherein R is a $C_1$–$C_4$ alkyl group, $R^1$ is an alkyl group having 15 to 17 carbon atoms, and $R^2$ and $R^3$ are hydrogen.

* * * * *